United States Patent [19]

Wood et al.

[11] Patent Number: 5,015,477

[45] Date of Patent: * May 14, 1991

[54] EDIBLE, BAKED COMPOSITIONS CONTAINING CHOLESTYRAMINE

[75] Inventors: Thomas G. Wood, Morris Plaines, N.J.; Carol J. Xenides, Fargo, N. Dak.

[73] Assignee: BASF K & F Corporation, Whippany, N.J.

[*] Notice: The portion of the term of this patent subsequent to Jun. 5, 2007 has been disclaimed.

[21] Appl. No.: 499,160

[22] Filed: Mar. 26, 1990

Related U.S. Application Data

[62] Division of Ser. No. 206,197, Jun. 13, 1988, Pat. No. 4,931,280.

[51] Int. Cl.$^5$ ................................................ A61K 9/00

[52] U.S. Cl. ..................................... 424/439; 424/440; 424/498; 424/78; 426/572; 426/618; 426/619; 426/620

[58] Field of Search ................. 424/439, 440, 498, 78; 426/572, 618, 619, 620

[56] References Cited

U.S. PATENT DOCUMENTS 4,931,280 6/1990 Wood et al. ......................... 424/439

Primary Examiner—Thurman Page
Assistant Examiner—William E. Benston, Jr.
Attorney, Agent, or Firm—Kenyon & Kenyon

[57] ABSTRACT

The edible baked composition delivers cholestyramine in a palatable, pleasant tasting form. Embodiments include a nutrition bar and a cookie. The composition is useful for the control of endogenous cholesterol levels in humans.

3 Claims, No Drawings

EDIBLE, BAKED COMPOSITIONS CONTAINING CHOLESTYRAMINE

CROSS REFERENCE TO RELATED APPLICATIONS

This application is a divisional application of U.S. application Ser. No. 206,197, filed June 13, 1988, now U.S. Pat. No. 4,931,280.

BACKGROUND OF THE INVENTION

The present invention relates to an edible, baked composition which will help control endogenous terol levels when ingested. More specifically, the composition contains cholestyramine which is useful in the control of cholesterol or lipid levels of the blood.

Hypercholesteremia, which is also known as high blood cholesterol level, is believed to be responsible in many cases for atherosclerosis. Therefore, it is exceedingly desirable to effect a reduction of the blood cholesterol level in adult, atherosclerotic patients. This has been done heretofore primarily through the use of low fat diets and medications. However, in many patients this is not sufficient to maintain the cholesterol within the desired limits. Accordingly, it is desirable to administer to the patient a cholesterol lowering agent.

Cholesterol and/or lipid reducing agents are useful in the treatment of arterial plaque formation (i.e. atherosclerosis). These medicinal agents, however, must be administered on a regular, periodic basis in order to exhibit their beneficial effects Moreover, when formulated as tablet, capsule or liquid dosages, these medicaments have the appearance and character of medicines used in the treatment of sickness and disease. Consequently, patients for whom cholesterol or lipid reducing agents have been prescribed will have an aversion toward routine, daily ingestion of such medicaments.

In particular, cholestyramine is a medicament of choice for the control of cholesterol or lipid levels in humans. Its administration, however, has proved to be problematic from a pharmaceutical compounding point of view. Not only does the cholestyramine exhibit an unpleasant taste and gritty oral consistency, but it is difficult to ingest and/or swallow under most conditions and methods employed to form masking pharmaceutical formulations.

Several attempts have been reported in the literature which attempt to circumvent these difficulties. For example, in EP86-300236, an ingestible anhydrous aggregate comprising starch, a non-cellulosic polysaccharide and cholestyramine is described. This aggregate is a candy which by reason of its extreme sweetness masks the unpleasant taste of the medicament involved. Another example, U.S. Pat. No. 3,974,272, also discloses an oral formulation containing cholestyramine. In this instance, the formulation has a base of milk or fruit juice and contains a hydrophilic colloid which masks the cholestyramine until it has passed the taste receptors along the human alimentary canal.

The sweetness and refined character of such candy confections containing medicaments like cholestyramine are not desirable for an edible medicament composition. The refined ingredients present do not deliver appropriate bulking character to the gut. These disadvantages detract or may, in certain instances, negate the advantage provided by the control of cholesterol level in the blood by cholestyramine.

It would be advantageous to develop a food product for administration of cholestyramine which also contains non-nutritive bulking agents. It would seem that such a food product could be adapted from so-called baked compositions. These baked compositions, however, require the use of high temperatures for congealing and solidifying their ingredients. The high temperature necessary for the baking in such instances will cause decomposition and degradation of cholestyramine. As a result, baked compositions of such ingredients as flour and solid sugars nave not been useful as vehicles for the oral administration of cholesterol and lipid control agents such as cholestyramine.

It is an object of the invention, therefore, to develop a baked composition containing cholestyramine which can be prepared at temperatures low enough to avoid or substantially eliminate the degradation and decomposition of cholestyramine. It is another object of the invention to develop a baked composition which is pleasant tasting, has a desirable oral constituency and which masks the unpleasant taste of cholestyramine. It is a further object of the invention to develop a baked composition which will deliver cholestyramine in a form that will enable efficient finding of bile salts and other cholesterol and lipid components present in the gut. Yet another object of the invention is to develop a medicinal formulation which will deliver a level of cholestyramine that will control cholesterol and lipid levels in humans.

SUMMARY OF THE INVENTION

These and other objects are achieved by the present invention which is directed to an edible, baked composition which is composed of a baked matrix of an edible oil, mono, oligo and polysaccharides, water, flavoring and cholestyramine which is present in an amount of about 5 to about 20% by weight relative to that of the composition.

The mono, oligo and polysaccharides present in the baked matrix include among others, an acid hydrolyzed starch binder which functions to form a congealed mass of the ingredients present in the baked matrix In specific part, the matrix ingredients are baked at a maximum temperature of about 150° C. to about 180° C. for no longer than about 20 minutes Yet they produce a firm baked composition because of the presence of the starch binder. Moreover, the cholestyramine present inside the baked matrix is substantially prevented from decomposing or degrading.

Under the preferred weight proportions of the oil, mono, oligo and polysaccharides, starch binder and cholestyramine present in the baked matrix, the cholestryamine and starch binder form a crisp, crunchy exterior and a sot chewy interior for the baked matrix.

Preferred embodiments include a baked matrix which contains a sweetening agent, a baked matrix which is formed from flour and optional leavening and non-cholesterol containing synthetic egg ingredients; a baked matrix having the form, texture and constituents characteristic of a cookie-like product; a baked matrix having the ingredients and characteristics of a nutritional bar-like composition; a baked matrix formed from all-natural ingredients; and a baked matrix containing oat bran which also controls endogenous cholesterol levels.

DETAILED DESCRIPTION OF THE INVENTION

The edible, medicinal composition of the present invention delivers reasonable levels of cholestyramine in the gut and will control cholesterol and lipid levels in humans when it is ingested on a regular basis. The medicinal composition is a pleasant tasting, orally ingestible substance which has additional nutritional and vitamin value. Its cookie-like or nutritional bar-like qualities make it a desirable means for administration of an otherwise unpleasant tasting medicament.

The baked matrix forming the medicinal composition of the invention contains a high proportion f cholestyramine as well as a starch binder. The starch binder, cholestyramine and other ingredients, such as the edible oil, combine during the baking process to readily undergo a crisping and congealing transformation similar to the Browning or Maillard reaction. The two ingredients, cholestyramine and starch binder, are believed to facilitate this low temperature baking so that the internal temperatures of the composition do not reach degradation or decomposition levels of cholestyramine during baking.

The saccharides of low to high molecular weights used as ingredients in the baked matrix include a starch binder, a starch, acid hydrolyzed starch, dextrins from high to moderate molecular weight, partially hydrolyzed dextrins of low to moderate molecular weight, simple and complex sugars such as glucose, lactose, fructose, raffinose, galactose, sucrose, invert sugar, honey, molasses, and other similar saccharides oligomers and polymers. In addition, artificial sweeteners such as saccharine, aspartame and other dipeptide sweeteners may be present.

The oligo and polysaccharides include amylose, amylopectin, polydextrins, oligodextrins of from 6 to 14 monomeric units in length, enzyme modified polydextrin, enzyme modified forms of the foregoing polysaccharides and acid and base hydrolyzed forms of the foregoing oligo and polysaccharides. Additional sugars useful as mono and oligo saccharides according to the invention include sorbose, allose, manose, iodose, talose, maltose and the like.

The edible oil employed as an ingredient in the baked matrix may be a saturated or unsaturated liquid fatty acid, its glyceride derivatives or fatty acid derivatives of plant or animal origin or a mixture thereof. Oils from natural sources that contain cholesterol and oils that the body will convert to cholesterol, however, are to be avoided. Palm oil, soybean oil, corn oil, saffron oil, sunflower seed oil, palmitic oil, linoleic oil, and hydrocarbon acid oils having chain lengths from C-10 to C-30 can be used as the oil ingredient of the baked matrix. Usually, a fatty glyceride compound derived from vegetable or marine oils or a synthetic produced congener thereof will comprise the edible oil used. Additional examples include lauroyl, myristoyl, stearoyl, oleoyl, behenoyl, arachidonoyl, erucoyl oils and the like. In addition to being obtained from the foregoing plant sources, these fats and oils may also be obtained from cotton seed, rape seed, peanut, olive, sesame, rice, wallflower, nasternum, mustard and other similar seed sources. Marine sources include whale, sardine, herring, menhaden and pilchard oils. Also included are di and triglycerides of the fatty glyceride compounds used as oils in the invention which can be the foregoing medium to long chain organic acids in combination with short chain organic acids such as acidic, propionic, butyric, valeric and caproic acids. Mixtures of the foregoing oils can also be used as the oil component according to the invention.

Additional ingredients present in the baked matrix according to the invention may be selected from cereals, rolled grains, nutmeats, peanut butter, cocoa, raisins, chocolate chips (e.g. those not including milk or dairy products), butterscotch chips, nutmeats including whole and chopped meats from edible nuts including walnuts, hickory nuts, hazel nuts, brazil nuts, peanuts, macadamia nuts, pecans, cashews, almonds and the like. Additionally, such nutmeat ingredients as fruits, dried fruits and cellulosic fibers, bran, ground bran, grain hulls, ground corn cobs and powdered bark can be used as additional ingredients in the composition. It is especially preferred that the composition contain oat bran. This bran can by itself control the sorption and resorption of cholsterol containing materials in the gut. Its combination with cholestyramine enhances this control effect of either the oat bran or the cholestyramine. Preservatives such as BHA, BHT and potassium sorbate may also be present. These ingredients provide nutrition, vitamins, bulking, ruffage and other similar desirable nutritious properties for the baked matrix according to the invention.

A preferred embodiment according to the invention is a cookie-like baked matrix. This embodiment can be formulated from flour, water, an optional leavening agent, acid hydrolyzed starch binder and edible oil, flavoring, and optional sweetening agent, and oligo and polysaccharides. The flour employed may be selected from wheat, oat, rice, soybean, corn, and other similar grain flours. The sweetening oligosaccharides may include honey, molasses, sucrose, invert sugar, fructose or mixtures thereof. The edible oil may include soybean oil, palm oil and triglycerides.

Another preferred embodiment is a nutritional bar-like composition formed as a baked matrix according to the invention. As in the cookie, this nutritional bar will contain such ingredients as the acid hydrolyzed starch binder, cholestyramine, edible oil and mono, oligo and polysaccharides. However, it will also include rolled grains, a lower amount of edible oil and, no flour, but rather solid mono and oligosaccharides such as sucrose, lactose, manose, maltose and dextrins and partially hydrolyzed dextrins.

It is preferred to have in both the cookie and bar portions of ruffage and bulking ingredients such as non-digestible cellulose, bran and the like. The presence of such ingredients helps lower cholesterol resorption in the gut and promotes bowel regularity.

Both the cookie and the nutritional bar can have crispy exteriors and doughy or chewy interiors. The texture of the cookie will be smooth while the texture of the nutritional bar will be composed of large particulate matter, some of which is non-nutritive and is bulk producing.

The weight ratios of ingredients present in the baked matrix medicinal composition according to the invention will in part determine the crispy exterior and the chewy interior of the composition. Moreover, the weight ratios of ingredients permit the congealment, gellation and transformation at a lower temperature relative to those baking temperatures typically used to produce baked products in this field. In general, it has been found that the weight ratio of edible oil to cholestyramine is from about 1:1 to about 1:4. The weight ratio of mono, oligo and polysaccharides to cholestyramine is from about 10:1 to about 2:1. In similar fashion, the weight ratio of acid hydrolyzed starch binder will be from 5 to 1 to about 1 to 1 relative to the weight of cholestyramine present. In general, the sum of the weights of the acid hydrolyzed starch binder and cholestyramine will be from about 10% to about 50 weight percent of the total composition. The weight ratio of edible oil to mono, oligo and polysaccharides will be from about 1:10 to about 1:2. In general, the acid hydrolyzed starch binder will comprise part of the mono, oligo an polysaccharides; however it may also be present alone or as a separate ingredient.

According to the invention, an especially preferred composition is a baked matrix nutrition bar composed of about 5 to 20 weight percent edible fiber, about 5 to 15 weight percent edible plant oil, about 5 to 25 weight percent polysaccharides selected from starch, dextrin, amylopectin, amylose, hydrolyzed or enzymatically treated forms thereof and mixtures thereof, about 20 to 30 weight percent acid hydrolyzed starch binder, about 10 to 25 weight percent mono or oligosaccharides selected from glucose, fructose, sucrose, invert sugar, lactose, maltose, galactose, hydrolyzed dextrins and mixtures thereof, about 5 to 20 weight percent rolled whole grains, about 5 to 15 percent water, about 5 to 20 percent cholestyramine, about 1 to 2 percent flavoring and spice and the remaining percentage of fruits, nuts, optional protein powder, vitamins and minerals. This composition has a pleasant taste and masks the off-taste of the cholestyramine. Moreover, in this nutrition bar, the exterior surfaces are crispy when the product has been baked at a temperature of about 150° C. for about 5 to 8 minutes. The interior is of a chewy texture.

Generally, this nutrition bar composition according to the invention will deliver to the gut an amount of cholestyramine sufficient for the efficient control of lipid and cholesterol level in the bloodstream when from 2 to 5 nutrition bars per day are consumed at regular intervals. In addition, the nutrition bar will deliver complex carbohydrates, protein, vitamins, minerals and other nutrients necessary or beneficial for daily activity. The level of cholestyramine present in the gut will be from about 3.5g to about 4.5g and will remain substantially constant during the periodic ingestion of the nutrition bar. It binds lipid, cholesterol and bile salt containing materials in the gut and permits their pass-through without sorption or resorption.

Another especially preferred composition according to the invention is a baked matrix cookie having a smooth cookie-like texture. This baked matrix cookie is composed of from about 5 to 15 weight percent edible plant oil, about 5 to 25 percent grain flour such as wheat, oat, rye or rice flour, about 20 to 30 weight percent acid hydrolyzed starch binder, about 5 to 20 weight percent sweetner selected from honey, molasses, sucrose, fructose, invert sugar or a mixture thereof, about 5 to 20 weight percent rolled whole grains, about 5 to 20 weight percent cholestyramine, about 2 to 15 weight percent water, flavoring, spice, optional protein powder, vitamins, minerals and other flavoring ingredients such as chocolate, butterscotch chips and nuts.

This cookie composition also delivers a desired level of cholestyramine to the gut when from approximately 2 to about 6 cookies per day are consumed at periodic intervals. In addition to the delivery of desired levels of cholestyramine, this preferred cookie composition delivers complex carbohydrates, vitamins, minerals and other nutrients necessary or beneficial for daily activity. Lipids, cholesterol and bile salts are thereby bound in the gut and their pass-through without sorption or resorption is permitted.

When the baked matrix according to the invention is to be prepared, the dry ingredients are blended together in a low speed mixing apparatus. These ingredients include the rolled grains, nuts, fruits, the solid mono, oligo and polysaccharides, and other dry ingredients. After the dry ingredients are thoroughly mixed, the fluid or viscous ingredients are combined. These include such ingredients as the edible oil, flavoring, spices, and mono and oligo saccharides such as honey, fructose, invert sugar and water. The combined ingredients are mixed in a low speed mixing apparatus for a period of time sufficient to produce a substantially homogeneous mixture. The acid hydrolyzed starch binder is combined with the mixture of dry and fluid or viscous ingredients after they have been combined into a substantial homogeneous combination.

Alternatively, the dry ingredients and the fluid or viscous ingredients can be combined separately. In this instance, the acid hydrolyzed starch binder will be added to the fluid, viscous mixed ingredients and stirred until a substantially homogeneous combination is produced. Then, the two mixtures are combined and mixed.

Following the thorough mixing of the foregoing ingredients, the appropriate selected amount of cholestyramine is added and the entire combination mixed at low speed for a time sufficient to produce a substantial homogeneous composition. The sticky, viscous composition then extruded as dollops by a wire cutter or other similar extruding apparatus onto a continuous or batch process baking sheets and placed into a baking oven for a time sufficient to cause the crisping reaction to occur on the exterior surfaces and to produce a chewy texture internally. The oven temperature employed will be from about 80~ to about 180~, preferably about 120~ to about 160~ C and most preferrably about 150~ C. The time for baking will approximately be from about 10 to about 20 minutes. Preferably about 14 to 18 minutes in time. It has been found that under these conditions the internal temperature of the baked matrix according to the invention does not reach a high enough temperature to cause decomposition or degradation of the cholestyramine present.

The invention will be further illustrated by the following examples. These examples, however, are not meant to limit the scope of the claims or the description of the invention presented in the foregoing specification.

EXAMPLE 1

Cholestyramine Nutritional Bar

The following dry ingredients were combined in a mixing bowl and mixed for approximately 3 minutes at low speed to produce a substantially homogeneous blend of dry ingredients. In a separate mixing bowl, the fluid and semi-viscous ingredients were combined and mixed at low speed to produce a substantially homogenous fluid mixture. The acid hydrolyzed starch binder having the tradename "Starch-Tender G" was combined with the fluid mixture and then further mixed on low speed for approximately 3 minutes until a substantially homogeneous combination was produced. The syrup mixture was added to the dry mixture while blending at low speed for approximately 5 minutes or until a substantially homogenous composition was produced. The sticky, semi-rigid dough was then extruded on a wire-cut machine into bar-like configurations and was baked for approximately 16 minutes at a temperature of about 145° C. to produce a crispy texture, a chewy interior nutritional bar.

The following list of ingredients and proportions were employed in the foregoing procedure to produce the nutritional bar described in this example.

| Ingredients | Weight % of Formulation |
| --- | --- |
| Rolled Oats | 3.6 Weight % |
| Oat Bran | 3.3 Weight % |
| Currant Raisins | 1.4 Weight % |
| Almonds | 1.4 Weight % |
| Soy Polysaccharides | 1.4 Weight % |
| Honey | 8.8 Weight % |
| Fructose | 55 Weight % |
| (Invert Sugar Composition) | 23.5 Weight % |
| Sugar (Sucrose) | 21.9 Weight % |
| Soybean Oil | 6.8 Weight % |
| Water | 8.5 Weight % |
| Cinnamon | 1 Weight % |
| Starch - Tender Gel G | 4 Weight % |
| Cholestyramine | 14.8 Weight % |
| Vanilla | 0.8% |

EXAMPLE 2

Composition and Procedure for Baked Cholestyramine Cookie Containing Flour

| Ingredient | Percent W/W | Ingredient | Percent W/W |
| --- | --- | --- | --- |
| Water | 30.7 | Unbleached Wheat Flour | 19.6 |
| White Sugar Sucrose | 5.5 | | |
| Brown Sugar Sucrose | 6.7 | Baking Soda | 0.3 |
| Soy Bean Oil | 9.2 | Salt | 0.1 |
| Molasses | 0.5 | Dates | 5.7 |
| Natural Brown Sugar Flavor | 0.1 | Oates | 3.5 |
| | | Medium Coconut Oil | 2.9 |
| Cinnamon | 0.1 | Sesame Seed | 2.0 |
| Narural Vanilla | 0.1 | Cholestyramine | 13.0 |
| | | | 100.0% |

The water, sugars, soy bean oil, molasses, vanilla, cinnamon and coconut oil for 5 minutes are mixed together and then the flour, baking soda and salt may be blended-in and mixed about 4 minutes. The dates, oats, sesame seeds and cholestyramine may be thereafter added and mixed about 3 minutes. The dough is measured into dollops to provide round cookies about 2 inches in diameter The dollops may be baked for about 14 minutes at about 300° F (about 150° C.) to provide the finished cookie.

EXAMPLE 3

Taste Testing

The Nutritional Bars described in Example 1 were manufactured on a large scale batch processing line and packaged in foil pouches under nitrogen The foil pouched Bars were stored at room temperature, 45° C., 37° C. and 75% relative humidity and refrigerated at 4° C. To determine their palatability and storage properties, these Bars were periodically taste-tested and checked for physical characteristics such as consistency, color, texture and mouth-feel by a four member taste panel. Samplings were made by the panel after one month and three months at 37° C. and 75% relative humidity, two months at 45° C, three months and six months at room temperature and six months refrigerated at 4° C. The panel determined that the taste and the physical characteristics of the Bars were acceptable at all sampling times under the conditions stated.

I claim:
1. An edible, baked composition in the form of a cookie suitable for medicinal use comprising:
   a baked matrix comprised of water, an edible oil, mono, oligo or polysaccharides, flavoring, and cholestyramine which is present in an amount of about 5 to 20 percent by weight relative to the weight of said composition,
   said composition being baked for a time period and at a temperature effective for providing a therapeutically effective dosage of undecomposed cholestyramine in said baked composition.
2. An edible, baked composition in the form of a nutritional bar comprising:
   a baked matrix comprised of water, an edible oil, mono, oligo or polysaccharides, flavoring, and cholestyramine which is present in an amount of about 5 to 20 percent by weight relative to the weight of said composition,
   said composition being baked for a time period and at a temperature effective for providing a therapeutically effective dosage of undecomposed cholestyramine in said baked composition.
3. A edible composition of claim 1 or 2 wherein the composition has a crispy exterior and a chewy interior.

* * * * *